United States Patent [19]

Kinnersley et al.

[11] Patent Number: 4,813,997

[45] Date of Patent: Mar. 21, 1989

[54] METHOD FOR REGULATING PLANT GROWTH

[75] Inventors: Alan M. Kinnersley, Knoxville, Tenn.; Taylor C. Scott, III; John H. Yopp, both of Carbondale, Ill.; George H. Whitten, Woodridge, Ill.

[73] Assignee: CPC International Inc., Englewood Cliffs, N.J.

[21] Appl. No.: 52,824

[22] Filed: May 22, 1987

Related U.S. Application Data

[63] Continuation-in-part of Ser. No. 34,191, Apr. 6, 1987, abandoned.

[51] Int. Cl.$^4$ .............................................. A01N 37/36
[52] U.S. Cl. ............................................ 71/66; 71/77; 71/106; 71/113; 47/1.4
[58] Field of Search ................... 71/66, 106, 113, 77; 47/1.4

[56] References Cited

U.S. PATENT DOCUMENTS

| | | | |
|---|---|---|---|
| 3,148,049 | 9/1964 | Herschler | 71/77 |
| 3,351,653 | 11/1967 | Carr et al. | 71/106 |
| 3,679,392 | 7/1972 | Strauss et al. | 71/113 |
| 4,471,077 | 9/1984 | Lange | 521/64 |

FOREIGN PATENT DOCUMENTS

| | | | |
|---|---|---|---|
| 1916054 | 10/1970 | Fed. Rep. of Germany | 71/113 |
| 0169404 | 9/1985 | Japan | 71/113 |
| 0193218 | 4/1967 | U.S.S.R. | 71/77 |

OTHER PUBLICATIONS

Zelitch, I., "The Relationship of Glycolic Acid to Respiration and, etc.", The Journal of Biological Chemistry, 234, No. 12, pp. 3077–3081, 1959.
Yamauchi et al., "Grafted Polyester Fibers", CA. 76, 128657f, 1972.
Bacskai, R., "Hot Melt Adhesive with Increased Heat, etc.", CA. 92, 42874t, 1980.
Ivanov et al., "Hydroxy Acids of Black Liquors", CA 80, 61258p, 1974.
Richards, E., "Degradation of Lactose by Interaction with, etc.", CA 64, 14477b, 1966.
Kirk-Othmer, Encyclopedia of Chemical Technology, 3rd Edit., vol. 13, pp. 80–82, 1981.
Mikami, et al., *Arg. Biol. Chem.*, 34, 977–979, (1970).

*Primary Examiner*—Richard L. Raymond
*Assistant Examiner*—Susan P. Treanor

[57] ABSTRACT

A process for increasing the rate of plant growth. Plants are treated with one or more acids, which are condensation products of glycolic and/or L-lactic acid. These acids also increase the concentration of chlorophyll, increase the rate of new plant formation when plants are propagated by tissue culture, decrease the amount of added nutrients required for plant growth, and protect plants against the toxic effects of salts. Certain of the acids are useful for increasing the rate of root formation in the plant.

17 Claims, No Drawings

METHOD FOR REGULATING PLANT GROWTH

This is a continuation-in-part of copending application, Ser. No. 034,191, filed Apr. 6, 1987 now abandoned.

FIELD OF THE INVENTION

The present invention relates to a process for increasing the rate of plant growth, increasing chlorophyll concentration, increasing rate of root formation, decreasing the amount of added nutrients required for plant growth, and protecting plants against the toxic effects of salts. In this process, plants are treated with dilute solutions of certain organic acids. These acids also increase the rate of new plant formation when plants are propagated by tissue culture.

BACKGROUND OF THE INVENTION

Various derivatives of organic acids have been proposed as plant growth regulators. For example, West German Pat. No. 19 16 054 discloses the use of alpha-hydroxy- or alpha-ketoalkanoic acids, having 7 to 10 carbon atoms, and their derivatives, particularly amides, for use for promoting the growth of plants under drought conditions. U.S. Pat. No. 3,148,049 discloses certain halogenated keto acids, such as halogenated acetoacetic acid, as plant growth regulators. U.S. Pat. No. 3,351,653 discloses the use of fluorinated hydroxy acids and esters as herbicides. In 1970, Mikami, et al, *Agr. Biol. Chem.*, 34, 977–979, reported test results of a number of hydroxy acids as plant growth regulators. Several of these, particularly, certain aromatic hydroxy acids, were shown to be root growth promoters. However, some of the simple acids, such as glycolic acid, caused suppression of root growth rather than root growth promotion. None of the hydroxy acids revealed any activity in the straight growth-promotion test used.

We have now discovered, to our surprise, that certain condensation polymers of the simple acids, glycolic acid and L-lactic acid, do act as growth promoters and have other advantages when applied to growing plants.

SUMMARY OF THE INVENTION

In accordance with this invention, there is provided a process for increasing the rate of growth of a plant which comprises supplying to the plant an effective amount of one or more acids having the following structural formula:

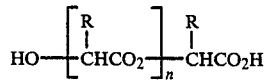   I where n is a small whole number from 1 to 10; the Rs are the same or different and denote H or $CH_3$; and if at least one R is $CH_3$, at least some of the asymmetric centers are in the L-configuration.

Further provided, in accordance with this invention, is a process for increasing the concentration of chlorophyll in a plant which comprises supplying to the plant an effective amount of one or more acids having the structural Formula I.

Also provided, in accordance with this invention, is a process for decreasing the amount of added nutrients required for growth of a plant which comprises supplying to the plant an effective amount of one or more acids having the structural Formula I.

Another provision, in accordance with this invention, is a process for protecting a plant against the toxic effects of salts which comprises supplying to the plant an effective amount of one or more acids having the structural Formula I.

In addition, in accordance with this invention, there is provided a process for enhancing the rate of formation of new plants when the plants are propagated by means of tissue culture which comprises culturing tissues of the plant on a growth medium which contains an effective amount of one or more acids having the structural Formula I.

Finally, in accordance with this invention, there is provided a process for increasing the rate of root formation of a plant which comprises supplying to the plant an effective amount of one or more acids having the following structural formula:

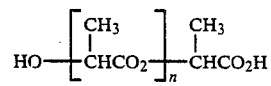   II where n is a small whole number from 1 to 10, and at least some of the asymmetric centers are in the L-configuration.

DETAILED DESCRIPTION OF THE INVENTION

The acids generally useful in the practice of this invention are the linear condensation polymers of lactic acid and glycolic acid. These may be obtained by condensing two or more molecules of the acids with the elimination of water. Mixed polymers of the two acids may also be used. When the polymers contain at least one lactic acid unit, at least some of the asymmetric centers must be in the L-configuration since polymers of D-lactic acid are not useful in this process.

The polymers having Formula I used in the process of this invention are readily obtained by heating the monomeric acids, preferably under reduced pressure. The mixtures of polymers so obtained can be used without further purification. If desired, the mixtures can be separated into their components by various fractionation techniques.

The activity of the acids used in the practice of this invention was discovered when they were tested in the duckweed promotion assay of Mitchell and Livingston, *Methods of Studying Plant Hormones and Growth-Regulating Substances*, USDA-ARS Agriculture Handbook, 336, pp. 66–67 (1968). This test showed that polymers having Formula I have growth-promoting abilities when used in the concentration of from between about 1 and about 1000 ppm (parts per million) on a weight/volume basis. Neither pure L-lactic acid nor pure D-lactic acid shows such growth-promoting properties. Likewise, the condensation polymers of D-lactic acid show little growth-promoting ability.

This growth-promoting ability of the polymers of L-lactic acid is even shown by the dimer of L-lactic acid, L-lactyl-L-lactic acid. It is also shown by the individual condensation polymers of L-lactic acid containing up to 10 lactic acid units.

Generally, when the concentration of nutrients present in the nutrient solution used for growing duckweed in the growth-promotion assay is reduced, the rate of duckweed growth is slower and a smaller plant yield is obtained. Surprisingly, if the polymers having Formula I are added to the growth medium, the amount of nutrients needed for good growth of the duckweed is greatly reduced. Thus, the use of these polymers not only enhances the growth of plants but also reduces the amount of nutrients which must be supplied to the plant.

An additional benefit derived from growing plants in the presence of polymers having Formula I is that the plants accumulate more chlorophyll. The presence of such polymers in the growth medium, particularly at the concentrations of from about 100 to about 1000 ppm on a weight/volume basis, greatly enhances the amount of chlorophyll accumulated per milligram of plant weight.

When the polymers having Formula I are supplied to plants, they enable the plant to grow in water containing concentrations of salts that would normally be toxic to the plants. This shows special utility for the process of this invention in applications using irrigation water of high salinity.

The growth-promoting ability of these polymers having Formula I are general properties as shown by their ability to enhance the growth of such diverse plants as lettuce, radishes, spinach, and corn. They are particularly useful in promoting the growth of plants in hydroponic culture.

The polymers having Formula I are also useful additives to tissue culture medium when plants are propagated by means of tissue culture. These acids enhance the formation of new shoots from the culture tissue, thus, increasing the rate of formation of new plants. Preferably they are used at a concentration between about 10 and about 1000 ppm on a weight/volume basis. This is a particularly useful property of these acids since many plants are now propagated commercially by means of tissue culture.

The polymers of L-lactic acid are also effective in increasing the rate of root formation in a plant. Plants grown in the presence of these acids have a considerable increase in average root length.

The acids used in the process of the present invention are thus seen to produce a wide variety of growth-regulant effects in the plants. The particular growth-regulant effect produced in a plant depends, of course, on a number of variables, including the acid or mixture of acids used, the concentrations and total amounts of the acids used, the time at which the acids are applied, and the type of plant species which is treated. The amount of material added is the effective amount needed to obtain the response desired.

In general, the acids are utilized in dilute aqueous solutions which contain the acids in concentrations of from about 1 to about 1000 ppm on a weight/volume basis. For most applications, the preferred concentrations are from about 10 ppm to about 100 ppm. However, for certain applications, the preferred ranges are from about 100 ppm to about 1000 ppm. The most suitable concentrations for a particular application are readily determined by well-known screening tests, such as those given in the examples.

Solutions of the acids are conveniently applied to the plants in the water added for plant growth. This water may also contain nutrients required by the plants. Optionally, solutions of the acids may be sprayed onto or otherwise applied to the roots, stems, or leaves of the plants.

The following specific examples illustrate the present invention. They are not intended to limit the invention in any way. When concentrations are given in ppm, they are on a weight/volume basis. When ratios of nitrogen, phosphorus, and potassium are given herein, they refer to the conventional fertilizer ratios in which the nitrogen is given as "weight % N", phosphorus is given as "weight % $P_2O_5$", and potassium is given as "weight % $K_2O$".

EXAMPLE 1

Duckweed (*Lemna minor* L.) was grown following the general procedure of Mitchell and Livingston, *Methods of Studying Plant Hormones and Growth Regulating Substances,* USDA-ARS Agriculture Handbook, 336, pp. 66–67 (1968). Plants were grown on Nickell's medium as described in the handbook with the iron being present as the ferrous ion chelated with EDTA. One plant at the three-frond stage was placed in each flask. Flasks were incubated in continuous light (500 lux) at 28±2° C. for 14 days. The plants were harvested and weighed. All reported values represent 3 to 5 replicates.

Experiments were performed in which 85% DL-lactic acid (Sigma Chemical Co.) was added at concentrations of 10, 100, and 1000 ppm. A control was run in which no acid was added. The results given in Table I demonstrate that growth is greatly enhanced when the lactic acid is present in the concentrations of 100 and 1000 ppm. This same effect was seen using DL-lactic acid from Fisher Scientific. The fact that pure D-lactic acid (Sigma Chemical Co., St. Louis, Mo.) and pure L-lactic acid (Fitz Chemical Co., Chicago, Ill.) do not give this growth enhancement is also shown by comparable experiments which are reported in Table I. It was discovered that the growth-promoting material in technical DL-lactic acid was due to larger molecules formed by condensation of 2 or more molecules of lactic acid. Growth is promoted by the simplest of such molecules, lactyllactic acid, formed by the condensation of 2 moles of lactic acid. This was demonstrated by testing L-lactyl-L-lactic acid obtained by the partial hydrolysis of the cyclic dimer of lactic acid, L-lactide (available from Henley and Co., New York City). The growth promotional property of this component is clearly shown by the results given in the last item of Table I.

TABLE I

| DUCKWEED GROWTH ASSAY | | | | |
|---|---|---|---|---|
| | Weight (mg) Added Acid (ppm) | | | |
| | Control | 10 | 100 | 1000 |
| DL-Lactic Acid (Technical 85%) | 130 ± 19[a] | 134 ± 7[a] | 207 ± 50[a] | 339 ± 56[a] |
| L-Lactic Acid (Pure) | 257 ± 28[a] | 256 ± 28[a] | 198 ± 64[a] | 175 ± 32[a] |
| D-Lactic Acid (Pure) | 71 ± 7[b] | 66 ± 4[b] | 75 ± 11[b] | 79 ± 5[b] |
| L-Lactyl-L-Lactic Acid | 46 ± 6[b] | 50 ± 15[b] | 71 ± 26[b] | 73 ± 21[b] |

[a]Fresh weight
[b]Dry weight

EXAMPLE 2

The general procedure given under Example 1 was followed. The acids used were mixed polymers of D- lactic acid, mixed polymers of L-lactic acid, and mixed polymers of DL-lactic acid. The polymers were obtained by heating the corresponding acids for 2½ hours at 100° C. under vacuum. The material was added to the duckweed flasks at the level of 1000 ppm. No lactic acid was added in the control. The results given in Table II show that the growth enhancement effect of the polymers of lactic acid is due to the polymers of L-lactic acid and is not exhibited by the polymers of D-lactic acid.

When duckweed was grown in the presence of poly-L-lactic acid uniformly labelled with carbon-14, it was found that 12% of the radioactive carbon was incorporated in the plant tissue. This indicates that the acid is acting as a true growth regulator.

TABLE II

EFFECT OF POLYLACTIC ACID ISOMERS ON DUCKWEED

| Treatment | Mean Dry Weight Per Flask (mg) |
| --- | --- |
| Control (No Acid) | 23 ± 2 |
| Poly-D-Lactic Acid | 28 ± 4 |
| Poly-L-Lactic Acid | 64 ± 7 |
| Poly-DL-Lactic Acid | 53 ± 10 |

EXAMPLE 3

The general procedure of Example 1 was followed in which various polymers of L-lactic acid were added to the duckweed growth medium. The amounts of polymers added were such as to give equivalent number of molecules in each flask. Dimer of lactic acid (DP2) was obtained by hydrolysis of L-lactide. Higher polymers of L-lactic acid containing from 4 to 6 lactic acid units (DP4-DP6) were obtained by heating the dimer of lactic acid under reduced pressure. They were separated by high-performance liquid chromatography (HPLC). The results given in Table III show that each of these polymers of L-lactic acid are growth promoters for duckweed and that the polymers containing 4 to 6 lactic acid units are somewhat more effective than the polymers containing 2 lactic acid units when they are used on an equimolar basis.

TABLE III

EFFECT OF L-LACTIC ACID POLYMERS ON DUCKWEED

| Additive | Dry Weight (mg) |
| --- | --- |
| Control (No Acid) | 70 ± 40 |
| DP2 (100 ppm) | 109 ± 11 |
| DP4 (200 ppm) | 149 ± 32 |
| DP5 (250 ppm) | 157 ± 15 |
| DP6 (300 ppm) | 156 ± 28 |

A similar experiment was run in which higher polymers of lactic acid (DP8, DP9, and DP10) were added to the growth medium for the duckweed. These showed similar enhancement of growth when they were used at equivalent molarities, i.e., 400, 450, and 500 ppm, respectively. When high concentrations (4000-5000 ppm) of these higher molecular weight polymers were added to the growth medium, the plants were very small and had tiny roots. This indicates that such polymers have promise in dwarfing or in growth management where slow growth is desired, such as in turf management.

EXAMPLE 4

Duckweed was also grown on media containing reduced amounts of Nickell's growth components, but, in each case, 100 ppm of L-lactyl-L-lactic acid was added to the mixture. In control experiments, duckweed was grown in reduced amounts of Nickell's growth medium components. The duckweed was grown and harvested in the usual manner, and the dry plants were then weighed. The results of these experiments given in Table IV show that the dimer of L-lactic acid produces excellent growth of the plants when only a fraction of the normal amount of nutrients is present. This shows that such polymers not only enhance growth of plants, but also reduce the amount of added nutrients required for growth.

TABLE IV

EFFECT OF L-LACTIC ACID DIMER ON DUCKWEED GROWN ON REDUCED NUTRIENTS

| Fraction of Nickell's Medium | Dry Weight (mg) | |
| --- | --- | --- |
| | Control | L-Lactyl-L-Lactic Acid (100 ppm) |
| 0 | 1 ± 1 | 1 ± 1 |
| 1/16 | 12 ± 2 | 25 ± 1 |
| 1/8 | 23 ± 1 | 48 ± 7 |
| 1/4 | 27 ± 3 | 46 ± 6 |
| Full Concentration | 30 ± 5 | 41 ± 12 |

EXAMPLE 5

The general procedure of Example 1 was followed using a mixture of polymers of glycolic acid, a mixture of polymers of L-lactic acid, and the dimer L-lactyl-L-lactic acid. The material was added to the duckweed flasks at levels of 10, 100, and 1000 ppm. The mixed polymers of glycolic acid were obtained by heating glycolic acid under vacuum (20 mm) at 85° C. for 21 hours. This mixture had about 27% glycolic acid, 20% DP2, 11% DP3, 20% DP4, 12% DP5, and smaller amounts of higher polymers of glycolic acid. (DP2=the dimer, DP3=the trimer, etc., of glycolic acid.) The mixed polymers of lactic acid were prepared in a similar manner to that used to make the polymers of glycolic acid. This mixture had about 28% lactic acid, 34% DP2, 22% DP3, 9% DP4, and smaller amounts of higher polymers of the lactic acid. The results given in Table V show that the mixed polymers of glycolic acid, the mixed polymers of L-lactic acid, the dimer L-lactyl-L-lactic acid all enhance growth of duckweed.

The duckweed grown in the presence of the acids appeared much darker green than that of the control. In order to measure chlorophyll content, duckweed was harvested, dried, suspended in 80% acetone, and homogenized for 30 seconds using a POLYTRON® brand homogenizer (Brinkman Instruments, Westbury, N.Y.). The mixture was centrifuged and absorption of the supernatant was read at 663 and 645 nm. From these readings, the number of micrograms of chlorophyll per milligram of dry weight was determined using the nomogram of Kirk, *Planta, 78, 200-207* (1968). The results also given in Table V show that the polymers of both lactic acid and glycolic acid increase chlorophyll content of the plants, particularly when present in the growth medium at from 100 to 1000 ppm.

The average length of the duckweed roots was measured for 50 plants grown in the controls and for 50 plants grown in the flasks containing 1000 ppm of each of the added acids. The results also given in Table V show that the polymers of lactic acid increase the root length.

TABLE V
COMPARISON OF GLYCOLIC ACID AND LACTIC ACID POLYMERS ON DUCKWEED GROWTH AND CHLOROPHYLL CONTENT

| Acid | Dry Weight (mg) | Chlorophyll (μg) Per mg | Root Length (mm) |
| --- | --- | --- | --- |
| Polyglycolic Acid | | | |
| 1000 ppm | 38.3 ± 3.5 | 5.5 | 8.5 ± 1.0 |
| 100 | 47.3 ± 2.1 | 5.7 | |
| 10 | 34.3 ± 2.5 | 2.4 | |
| Poly-L-Lactic Acid | | | |
| 1000 ppm | 76.3 ± 11.3 | 6.5 | 13.7 ± 3.2 |
| 100 | 46.3 ± 5.8 | 2.7 | |
| 10 | 27.3 ± 2.3 | 2.1 | |
| L-Lactyl-L-Lactic Acid | | | |
| 1000 ppm | 39.3 ± 7.6 | 6.0 | 10.1 ± 1.7 |
| 100 | 46.3 ± 10.0 | 4.5 | |
| 10 | 28.0 ± 4.3 | 1.6 | |
| Control (No Acid) | 20.0 ± 2.5 | 2.0 | 7.7 ± 2.0 |

EXAMPLE 6

The general procedure of Example 5 was followed except that the material added to the duckweed flasks was a copolymer prepared by heating an equimolar mixture of glycolic acid and L-lactic acid for 90 minutes under reduced pressure. The procedure was repeated using physical mixtures of glycolic and lactic acid polymers containing two different proportions of the poly acids. These were the same polymers used in Example 5. The results of these tests given in Table VI show that both physical mixtures of the polymers and copolymers of the acids enhance growth of duckweed.

TABLE VI
EFFECT OF MIXED POLYMERS OF GLYCOLIC AND LACTIC ACIDS ON DUCKWEED GROWTH

| Acid | Dry Weight (mg) |
| --- | --- |
| Copolymer of Glycolic Acid and L-Lactic Acid | |
| 1000 ppm | 56.5 ± 9.7 |
| 100 | 48.0 ± 6.9 |
| 10 | 38.7 ± 2.9 |
| Control (No Acid) | 35.5 ± 10.5 |
| 1:1 Mixture of Polymers of L-Lactic Acid and Glycolic Acid | |
| 1000 ppm | 43.7 ± 6.9 |
| 100 | 37.5 ± 3.4 |
| 10 | 27.7 ± 1.9 |
| 3:1 Mixture of Polymers of L-Lactic Acid and Glycolic Acid | |
| 1000 ppm | 56.0 ± 10 |
| 100 | 44.0 ± 9.5 |
| 10 | 30.7 ± 6.8 |
| Control (No Acid) | 23 ± 3.8 |

EXAMPLE 7

Fine vermiculite (125 ml) was placed in a 1-liter Erlenmeyer flask capped with a silicone foam closure. Then 100 ml of a nutrient solution containing 0.5 g/l MIRACLE-GRO ® (a plant food having an N:P:K ratio of 15:30:15) was added. In addition to the nutrient solution, L-lactyl-L-lactic acid at 100 or 1000 ppm was placed in certain flasks. Twelve radish seeds (Var. "Scarlet Globe", Yopp Quality Seeds, Carbondale, Ill.) were planted in each flask. After 10 days, all plants in each flask were pooled, dried, and weighed. The plants grown on the medium containing 1000 ppm of L-lactyl-L-lactic acid had an average dry weight (average of 4 flasks) of about 30% greater than that of the plants grown on the same medium, but containing none of the lactic acid dimer. The plants grown on medium containing 100 ppm of the lactic acid dimer had an average dry weight about 5% greater than that of the controls.

The experiment with radish seeds was repeated except that the lactic acid dimer was replaced by varying concentrations (10, 100 and 1000 ppm) of the mixture of L-lactic acid polymers used in Example 5. Plants were grown for 16 days before they were harvested. The plants grown on a medium containing 1000 ppm of the mixture of lactic acid polymers on the average weighed about 20% more than those grown on the nutrient medium without any lactic acid polymers. The shoots of the radishes grown on the medium containing the lactic acid polymers also contained about 30% more chlorophyll per milligram of dry weight than did the corresponding shoots of radishes grown on the control medium which contained no lactic acid polymers. These results clearly show the ability of the lactic acid polymers to increase the growth and chlorophyll content of radishes.

EXAMPLE 8

Corn was planted in 15-cm diameter pots filled with an autoclaved mixture of greenhouse potting soil and field soil. Fertilizer solution having an N:P:K ratio of 4:2:2 was diluted with water so that it was applied at a rate of 28 kg of nitrogen/hectare when 100 ml was added per pot. Four seeds of George W. Park Seed Company's 5145 Trucker's Favorite White Corn were planted in each pot in the greenhouse. The pots were watered twice a week. After 1 week, the pots were thinned to two plants per pot. One hundred ml of a solution containing varying concentrations of L-lactic acid dimer, adjusted to pH 6.6, was added each week for 4 weeks. The plants were then allowed to grow for an additional month with watering but without the addition of more lactic acid dimer. Since the experiments were run in the winter, the existing light was supplemented with 320 watts of fluorescence light. Plants were then harvested, dried, and weighed. The results given in Table VII show that the dimer of L-lactic acid stimulates the early growth of corn plants when it is added at a concentration of from 1 to 10 ppm per treatment. Higher concentrations of the lactic acid dimer give less stimulation of plant growth. When radish seeds were grown under these conditions with varying amounts of the L-lactic acid dimer, no significant effect on growth was observed. However, the lactic acid dimer did promote growth of radishes under slightly different conditions (Example 7).

TABLE VII
EFFECT OF L-LACTIC ACID DIMER ON GROWTH OF CORN

| Acid Added (ppm) | Total Plant Mean Dry Weight (g) |
| --- | --- |
| None (Control) | 0.45 ± 0.07 |
| 1 | 0.94 ± 0.07 |
| 10 | 1.2 ± 0.2 |
| 100 | 0.64 ± 0.07 |

EXAMPLE 9

Spinach seeds were germinated in a mixture of peat moss, vermiculite, and perlite. After 9 days, seedlings were transferred to hydroponic units. Lettuce seeds were germinated on filter paper discs wet with distilled water. After 3 days, seedlings were transferred to hydroponic units. The units used were Jewel-Hubbard Scientific (Carolina Biological Supply Co., Burlington, N.C.) single-hydroponic units filled with 18.5 liters of medium. The medium used had the following composition:

|  | Concentration Per Liter |
|---|---|
| $KH_2PO_4$ | 0.034 g |
| $KNO_3$ | 0.127 g |
| $Ca(NO_3)_2.4H_2O$ | 0.296 g |
| $MgSO_4.7H_2O$ | 0.124 g |
| $H_3BO_3$ | 0.72 mg |
| $MnCl_2.4H_2O$ | 0.45 mg |
| $ZnSO_4.7H_2O$ | 0.055 mg |
| $CuSO_4.5H_2O$ | 0.020 mg |
| $NaMoO_4.2H_2O$ | 0.007 mg |
| $FeSO_4.7H_2O$ | 0.68 mg |
| $Na_2EDTA$ | 0.93 mg |

The medium flow rate was 80 ml/min with no aeration of the reservoir tank. Fresh medium, adjusted to pH 6.0, was added each week. To certain of the hydroponic units was added the dimer of L-lactic acid at a concentration of 100 ppm.

Spinach was harvested 38 days after germination, lettuce was harvested 30 days after germination. The fresh weight of individual plants was recorded, and all plants for each treatment were then pooled and dried at 70° C. for 16 hours for a single total dry weight for each treatment. The results given in Table VIII show that the dimer of L-lactic acid, when employed at a concentration of 100 ppm, is effective in stimulating the growth of both spinach and lettuce when grown hydroponically.

TABLE VIII
EFFECT OF L-LACTIC ACID DIMER ON SPINACH AND LETTUCE GROWN HYDROPONICALLY

|  | Mean Weight Per Plant (g) | |
|---|---|---|
|  | Fresh Weight | Dry Weight |
| Spinach |  |  |
| Control | 6.1 ± 2 | 0.41 |
| 100 ppm Acid | 9.2 ± 2 | 0.63 |
| Lettuce |  |  |
| Control | 1.6 ± 0.4 | 0.083 |
| 100 ppm Acid | 4.1 ± 0.7 | 0.20 |

EXAMPLE 10

Potato shoot cultures were initiated from shoot tips excised from "eyes" of potato tubers. Excised shoot tips, consisting of apical domes accompanied by 4- to 6-leaf primordia, were placed upon nodal propagation medium. This medium consisted of Murashige and Skog salts (*Physiol. Plant.*, 15, 473–497 (1962)) plus 30 g/l sucrose, 0.4 mg/l thiamine, 100 mg/l i-inositol, and 0.17 g/l $NaH_2PO_4.H_2O$.

Ten replicate tubes were each inoculated with a single shoot. Each tube (25×150 mm) contained 20 ml of medium, which was adjusted to pH 6.0 and solidified with 1% agar. Sealed tubes were kept under 16 hr/day light at about 5000 lux at a constant 25° C. Thirty days after inoculation, the shoots were counted and recorded. The contacts of each tube was cut into sections with each section containing a single shoot. These shoots were than transferred to fresh media. After an additional 30 days, the number of shoots was again counted. The experiments were repeated with two levels of the dimer of L-lactic acid added to the medium and two levels of a mixed polymer of L-lactic acid added to the medium. When the dimer of L-lactic acid or the mixed polymers of L-lactic acid were added to the tissue culture medium at levels from 100 to 1000 ppm, the number of shoots produced increased by from 5% to 20% over those of the controls. Mixed polymers of L-lactic acid were somewhat more effective than the dimers of L-lactic acid in this promotion.

The general procedure outlined for potato shoot cultures was followed for shoot primordial cultures of tobacco. The plantlets grown in media containing 50 ppm and 100 ppm of mixed polymers of L-lactic acid showed increases in weights over those of the control of 20% and 50%, respectively. Higher concentrations of the polymers of lactic acid in the medium (500–1000 ppm) inhibited growth of the cultures but gave products with a higher concentration of chlorophyll.

These examples show that the polymers of L-lactic acid are useful in enhancing the rate of formation of new plants when the plants are propagated by means of tissue culture.

EXAMPLE 11

Duckweed was grown using the general procedure of Example 1. Plants were grown in control flasks which contained only the culture medium. Other plants were grown in flasks containing medium to which was added 400 ppm of $Mn^{++}$ (as $MnSO_4.H_2O$) with and without added polyglycolic acid, poly-L-lactic acid, or L-lactyl-L-lactic acid. The results given in Table IX show that the dimer of lactic acid as well as the polymers of lactic and glycolic acids are able to protect duckweed from the growth-inhibiting effects of the manganous ion. It is noted that the preferred concentrations of polyglycolic acid and L-lactyl-L-lactic acid for this purpose are about 100 ppm, whereas, the preferred concentration of poly-L-lactic acid is about 1000 ppm for this purpose.

TABLE IX
EFFECT OF VARIOUS ACIDS ON DUCKWEED GROWN IN PRESENCE OF $Mn^{++}$

| Additives | Mean Dry Weight Per Flask (mg) |
|---|---|
| Control | 27.0 ± 3.3 |
| 400 ppm $Mn^{++}$ | 6.5 ± 1.3 |
| 400 ppm $Mn^{++}$ + 1000 ppm PGA[a] | 2.2 ± 0.5 |
| 400 ppm $Mn^{++}$ + 100 ppm PGA | 41.0 ± 7.4 |
| 400 ppm $Mn^{++}$ + 10 ppm PGA | 12.0 ± 2.6 |
| Control | 23.8 ± 4.8 |
| 400 ppm $Mn^{++}$ | 12.9 ± 2.8 |
| 400 ppm $Mn^{++}$ + 1000 ppm PLA[b] | 95.7 ± 9.8 |
| 400 ppm $Mn^{++}$ + 100 ppm PLA | 33.0 ± 2.8 |
| 400 ppm $Mn^{++}$ + 10 ppm PLA | 17.4 ± 1.9 |
| Control | 35.5 ± 7.5 |
| 400 ppm $Mn^{++}$ | 12.5 ± 2.4 |
| 400 ppm $Mn^{++}$ + 1000 ppm LL[c] | All dead |
| 400 ppm $Mn^{++}$ + 100 ppm LL | 51.2 ± 8.6 |
| 400 ppm $Mn^{++}$ + 10 ppm LL | 17.2 ± 5.3 |

[a]PGA = Polyglycolic acid mixture having the composition given in Example 5.
[b]PLA = Poly-L-lactic acid mixture having the composition given in Example 5.
[c]LL = L-lactyl-L-lactic acid.

EXAMPLE 12

The general procedure of Example 11 was followed except that plants were grown in flasks containing medium with various levels of $Cu^{++}$ (as $CuSO_4.5H_2O$) and seawater with and without added L-lactic acid polymers. The results given in Table X show the effectiveness of L-lactic acid polymers in protecting the plants against the growth-inhibiting effects of the copper ion and of the mixture of ions present in seawater.

In a similar experiment, it was shown that 10 to 100 ppm of the L-lactic acid dimer protected the plants from the growth-inhibiting effect of 15% seawater. However, a growth medium containing 1000 ppm of the lactic acid dimer and 15% seawater was toxic to the plants.

TABLE X
EFFECT OF L-LACTIC ACID POLYMERS ON DUCKWEED GROWN IN PRESENCE OF SALTS

| Additives | Mean Dry Weight Per Flask (mg) |
|---|---|
| Control | 56.0 ± 7.3 |
| 6.25 ppm $Cu^{++}$ | 31.7 ± 4.0 |
| 6.25 ppm $Cu^{++}$ + 1000 ppm PLA[a] | 87.2 ± 5.7 |
| 12.5 ppm $Cu^{++}$ | 16.5 ± 3.1 |
| 12.5 ppm $Cu^{++}$ + 1000 ppm PLA | 63.5 ± 3.1 |
| 18.75 ppm $Cu^{++}$ | All dead |
| 18.75 ppm $Cu^{++}$ + 1000 ppm PLA | All dead |
| 7.5% Seawater[b] | 46.0 ± 8.5 |
| 7.5% Seawater + 1000 ppm PLA | 103.0 ± 8.8 |
| 15% Seawater | 31.0 ± 2.8 |
| 15% Seawater + 1000 ppm PLA | 46.0 ± 5.3 |
| 22.5% Seawater | 10.7 ± 1.7 |
| 22.5% Seawater + 1000 ppm PLA | 16.3 ± 2.5 |

[a]PLA = Poly-L-lactic acid mixture having the composition given in Example 5.
[b]MARINEMIX ®, a salt mixture containing 29 different ions (Marine Enterprises, Baltimore, Md.), was dissolved in sufficient distilled water to give the specified percent of seawater concentration.

EXAMPLE 13

Chlorella vulgaris was grown in Chu-Gerloff medium (Gerloff, et al, pp. 27–44, in *The Culturing of Algae: A Symposium*, Antioch Press, Yellow Springs, Ohio (1950)) in 250-ml Erlenmeyer flasks sealed with rubber closures. The flasks were shaken at 40 rpm and exposed to about 4000 lux of light for 16 hrs per day. After 8 days of growth, 5-ml samples of each culture were dried, and the chlorophyll content of the cells was measured using the procedure given in Example 5. Tests were repeated on chlorella grown in the presence of added poly-L-lactic acid, and on chlorella grown in the presence of seawater with and without added poly-L-lactic acid. The results given in Table XI are the averages of determinations made on contents of four different flasks at each concentration level. They demonstrate the ability of lactic acid polymers to increase the amount of the metabolite, chlorophyll, even when the algae are grown in the presence of substantial concentrations of the salts found in seawater.

TABLE XI
EFFECT OF L-LACTIC ACID POLYMERS ON CHLOROPHYLL CONTENT OF CHLORELLA GROWN IN PRESENCE OF SALTS

| Additives | Chlorophyll µg/ml Extractant |
|---|---|
| Control | 2.8 ± 0.3 |
| 1000 ppm PLA[a] | 8.1 ± 0.2 |
| 25% Seawater[b] | 2.7 ± 2.3 |
| 25% Seawater + 1000 ppm PLA | 6.6 ± 1.1 |
| 30% Seawater | 1.7 ± 0.4 |
| 30% Seawater + 1000 ppm PLA | 6.1 ± 1.0 |

[a]PLA = Poly-L-lactic acid mixture having the composition given in Example 5.
[b]MARINEMIX ®, a salt mixture containing 29 different ions (Marine Enterprises, Baltimore, Md.), was dissolved in sufficient distilled water to give the specified percent of seawater concentration.

Thus, it is apparent that there has been provided, in accordance with the invention, an improved process for increasing the rate of plant growth, for increasing root growth and the chlorophyll content, for protecting a plant against the toxic effects of salts, for decreasing the amount of added nutrients required for growth of a plant, and for enhancing the rate of formation of new plants when the plants are propagated by means of tissue culture, which fully satisfies the objectives, aims, and advantages set forth above. While the invention has been described in conjunction with specific embodiments thereof, it is evident that many alternatives, modifications, and variations will be apparent to those skilled in the art in light of the foregoing description. Accordingly, it is intended to include all such alternatives, modifications, and variations as set forth within the spirit and scope of the appended claims.

What is claimed is:

1. A process for increasing the rate of growth of a plant which comprises supplying to the roots, stems and foliage of the plant an effective amount of one or more acids having the structural formula:

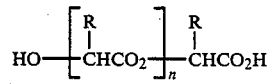

where n is a whole number from 1 to 10; the Rs are the same or different and denote H or $CH_3$; and if at least one R is $CH_3$, at least some of the asymmetric centers are in the L-configuration.

2. The process of claim 1 wherein the acid is supplied to the plant in an aqueous solution at a concentration of between about 1 and about 1000 parts per million on a weight/volume basis.

3. The process of claim 1 wherein the plant is *Lemna minor* L.

4. The process of claim 1 wherein th plant is selected from the group: lettuce, spinach, and corn.

5. The process of claim 4 wherein the plant is grown in hydroponic culture.

6. A process for increasing the concentration of chlorophyll in a plant which comprises supplying to the roots, stems and foliage of the plant an effective amount of one or more acids having the structural formula:

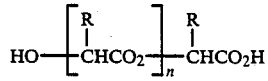

where n is a whole number from 1 to 10; the Rs are the same or different and denote H or $CH_3$; and if at least one R is $CH_3$, at least some of the asymmetric centers are in the L-configuration.

7. The process of claim 6 wherein the acid is supplied to the plant in an aqueous solution at a concentration of between about 100 and about 1000 parts per million on a weight/volume basis.

8. The process of claim 6 wherein the plant is selected from the group: *Lemna minor* L. and *Chlorella vulgaris*.

9. A process for increasing the rate of root formation in a plant which comprises supplying to the roots, stems and foliage of the plant an effective amount of one or more acids having the structural formula:

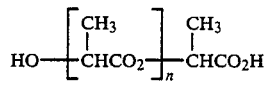

where n is a whole number from 1 to 10, and at least some of the asymmetric centers are in the L-configuration.

10. The process of claim 9 wherein the acid is supplied to the plant in an aqueous solution at a concentration of between about 1 and about 1000 parts per million on a weight/volume basis.

11. The process of claim 9 wherein the plant is selected from the group: *Lemna minor* L., lettuce, and corn.

12. A process for decreasing the concentration of the basic nutrient medium required for growth of a plant which comprises supplying to the roots, stems or foliage of the plant an effective amount of one or more acids having the structural formula:

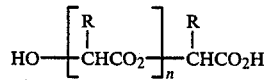

where n is a whole number from 1 to 10; the Rs are the same or different and denote H or $CH_3$; and if at least one R is $CH_3$, at least some of the asymmetric centers are in the L-configuration.

13. The process of claim 12 wherein the acid is supplied to the plant in an aqueous solution at a concentration of between about 1 and about 1,000 parts per million on a weight/volume basis.

14. The process of claim 12 wherein the plant is *Lemna minor* L.

15. A process for protecting a plant against the toxic effects of salts which comprises supplying to the roots, stems and foliage of the plant an effective amount of one or more acids having the structural formula:

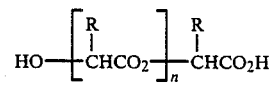

where n is a whole number from 1 to 10; the Rs are the same or different and denote H or $CH_3$; and if at least one R is $CH_3$, at least some of the asymmetric centers are in the L-configuration.

16. The process of claim 15 wherein the acid is supplied to the plant in an aqueous solution at a concentration of between about 1 and about 1000 parts per million on a weight/volume basis.

17. The process of claim 15 wherein the plant is selected from the group: *Lemna minor* L. and *Chlorella vulgaris*.

* * * * *

REEXAMINATION CERTIFICATE (2626th)
United States Patent [19]
Kinnersley et al.

[11] B1 4,813,997
[45] Certificate Issued Jul. 18, 1995

[54] METHOD FOR REGULATING PLANT GROWTH

[75] Inventors: Alan M. Kinnersley, Knoxville, Tenn.; Taylor C. Scott, III; John H. Yopp, both of Carbondale, Ill.; George H. Whitten, Woodridge, Ill.

[73] Assignee: CPC International Inc., Englewood Cliffs, N.J.

Reexamination Requests:
No. 90/003,035, Apr. 27, 1993
No. 90/002,306, Mar. 26, 1991

Reexamination Certificate for:
Patent No.: 4,813,997
Issued: Mar. 21, 1989
Appl. No.: 52,824
Filed: May 22, 1987

Related U.S. Application Data

[63] Continuation-in-part of Ser. No. 34,191, Apr. 6, 1987, abandoned.

[51] Int. Cl.$^6$ ............................................. A01N 37/36
[52] U.S. Cl. ................................. 504/157; 504/142; 504/313; 47/1.4
[58] Field of Search .................... 71/66, 77, 106, 113; 47/1.4; 504/142, 157, 313

[56] References Cited

U.S. PATENT DOCUMENTS

| | | | |
|---|---|---|---|
| 4,313,752 | 2/1982 | Siemer | 71/27 |
| 4,473,648 | 9/1984 | Tang | 435/240 |
| 4,536,474 | 8/1985 | Yamamoto et al. | 435/42 |
| 4,554,252 | 11/1985 | Farkas et al. | 435/240 |
| 4,626,277 | 12/1986 | Suzuki et al. | 71/113 |
| 4,634,674 | 1/1987 | Shahin | 435/240 |
| 4,863,506 | 9/1989 | Young | 71/113 |

FOREIGN PATENT DOCUMENTS

| | | |
|---|---|---|
| 0157167 | 12/1975 | Japan. |
| 3069164 | 6/1978 | Japan. |
| 9010501 | 1/1984 | Japan. |
| 0013703 | 1/1985 | Japan. |
| 1060163 | 1/1982 | U.S.S.R.. |

OTHER PUBLICATIONS

Zelitch, I., "Biochemical Control of Stomatal Opening and the Synthesis of Glycolic Acid in Leaves", Federation Proceedings, vol. 24, p. 980, 1965.
Die Makromolekulare Chemie, vol. 37, 1960, pp. 64–70, Basel, CH; A. Schoberl: "Über Polythioglykolide".
Die Makromokekulare Chemie, vol. 140, (no. 3429), 1970 pp. 41–54, Basel, CH; H. G. Buhrer et al.: "Polythiolester II. Polythiolactid".
Justus Liebigs Annalen Der Chemie, 595, 1955, p. 110.
PCT International Search Report dated Jul. 14, 1988.
Fresenius, P. Organic Chemical Nomenclature. pp. 196–198.
Kirk–Othmer Encyclopedia of Chemical Technology 3rd ed. vol. 13. pp. 80–82. 1981.
Ueda et al. Fermentation Engineering Journal. No. 36. Report II. p. 368–371. 1958.
The Merck Index 1983.
Encyclopedia of Polymer Science and Engineering. vol. 12, "Polyesters". pp. 1–9, 36–39. 1988.
Leopold et al. Plant Growth and Development. NY: McGraw–Hill Book Co. 1975. pp. 9–10.
Kirk–Othmer, "Encyclopedia of Chemical Technology", pp. 80–82, (Third Edition). vol. 13, 1981.
Ueda (I) "The Composition of Commercial Grade Lactic Acid", Fermentation Engineering Journal, No. 36, pp. 368–371, 1958 (Translation).
Ueda (II); "The Chance of Lactic Acid Polmers by Dilution", Fermentation Engineering Journal, No. 36, pp. 371–374, 1958 (Translation).

Primary Examiner—S. Mark Clardy

[57] ABSTRACT

A process for increasing the rate of plant growth. Plants are treated with one or more acids, which are condensation products of glycolic and/or L-lactic acid. These acids also increase the concentration of chlorophyll, increase the rate of new plant formation when plants are propagated by tissue culture, decrease the amount of added nutrients required for plant growth, and protect plants against the toxic effects of salts. Certain of the acids are useful for increasing the rate of root formation in the plant.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

claims 1-17 are cancelled.

* * * * *